United States Patent
Fadler

(10) Patent No.: US 8,457,278 B2
(45) Date of Patent: Jun. 4, 2013

(54) RADIATION THERAPY DEVICE

(75) Inventor: Franz Fadler, Hetzles (DE)

(73) Assignee: Siemens Aktiengesellschaft, München (DE)

( * ) Notice: Subject to any disclaimer, the term of this patent is extended or adjusted under 35 U.S.C. 154(b) by 232 days.

(21) Appl. No.: 12/829,935

(22) Filed: Jul. 2, 2010

(65) Prior Publication Data

US 2011/0007865 A1    Jan. 13, 2011

(30) Foreign Application Priority Data

Jul. 9, 2009 (DE) .......................... 10 2009 032 429

(51) Int. Cl.
*A61N 5/00* (2006.01)

(52) U.S. Cl.
USPC ............................................. 378/65; 378/62

(58) Field of Classification Search
USPC .............................................. 378/65, 64, 62
See application file for complete search history.

(56) References Cited

U.S. PATENT DOCUMENTS

| | | |
|---|---|---|
| 7,227,925 B1 | 6/2007 | Mansfield et al. |
| 7,502,443 B1 | 3/2009 | Haynes et al. |
| 2003/0048868 A1* | 3/2003 | Bailey et al. .................... 378/65 |
| 2006/0193435 A1* | 8/2006 | Hara et al. ...................... 378/65 |
| 2008/0197304 A1 | 8/2008 | Urano et al. |
| 2008/0267352 A1 | 10/2008 | Aoi et al. |
| 2009/0086889 A1* | 4/2009 | Hashemi et al. ................ 378/22 |
| 2009/0161818 A1 | 6/2009 | Sakurai et al. |
| 2009/0296886 A1* | 12/2009 | Maltz et al. ..................... 378/65 |

FOREIGN PATENT DOCUMENTS

DE    102007018288 A1    10/2008

OTHER PUBLICATIONS

German Office Action dated Mar. 19, 2010 for corresponding German Patent Application No. De 10 2009 032 429.1 with English translation.
German Office Action dated Jun. 18, 2010 for corresponding German Patent Application No. De 10 2009 032 429.1 with English translation.

* cited by examiner

*Primary Examiner* — Hoon Song
(74) *Attorney, Agent, or Firm* — Lempia Summerfield Katz LLZ

(57) ABSTRACT

A radiation therapy device includes a radiation application apparatus, which is used to direct a therapeutic beam along a therapeutic beam center axis onto a target volume to be irradiated. The radiation therapy device also includes a diagnostic radiation source for diagnostic x-ray radiation, is the diagnostic radiation source being disposed eccentrically in relation to the therapeutic beam center axis in a rotatable manner on a rotation apparatus so that the diagnostic radiation source is operable to be rotated about the therapeutic beam center axis. The radiation therapy device further includes a detector for diagnostic x-ray radiation, which is used to detect the diagnostic x-ray radiation emitted from the diagnostic radiation source.

19 Claims, 5 Drawing Sheets

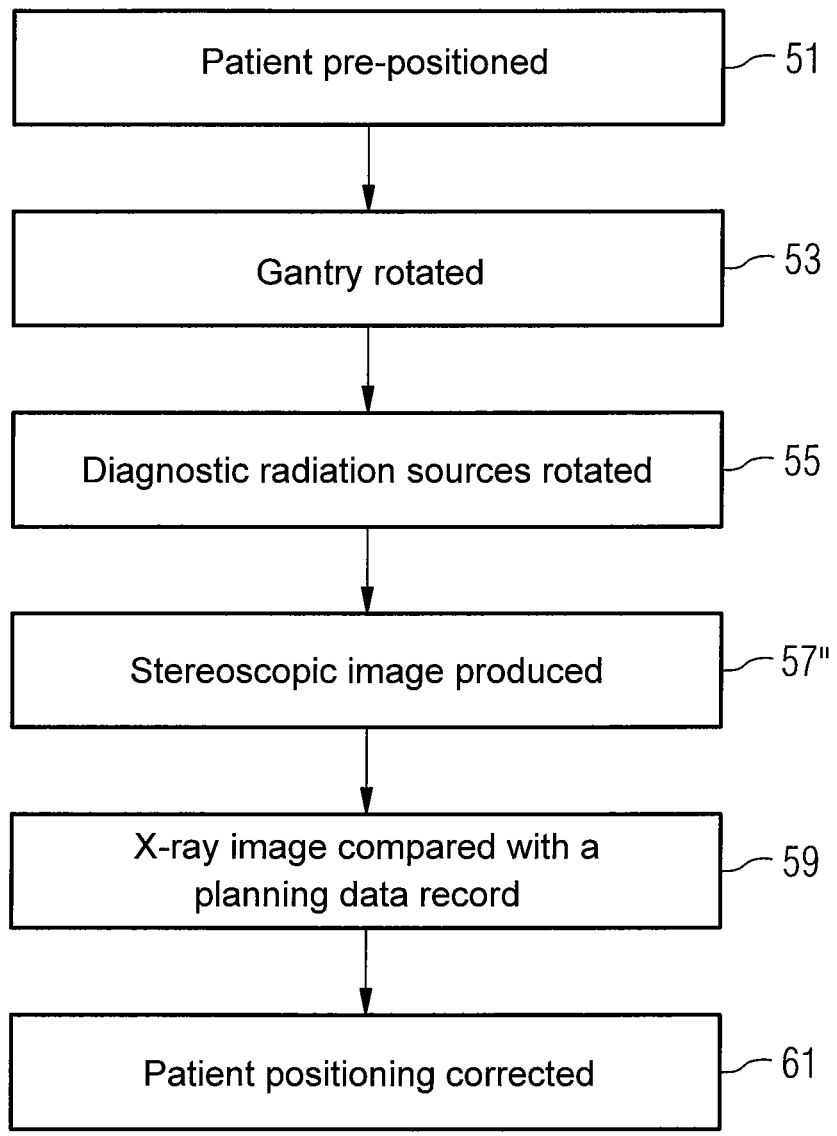

8,457,278 B2

RADIATION THERAPY DEVICE

This application claims the benefit of DE 10 2009 032 429.1, filed on Jul. 9, 2009, which is hereby incorporated by reference.

BACKGROUND

The present embodiments relate to a radiation therapy device.

Radiation therapy is an established method that is used, in particular, for treating tumors. Radiation therapy devices that have a radiation application apparatus, which can be used to direct a therapeutic beam onto a patient to be treated, are known.

Some of these radiation therapy devices also include an imaging apparatus, in which a diagnostic radiation source and a diagnostic radiation detector are employed. The diagnostic radiation source emits diagnostic x-ray radiation, which is recorded by the radiation detector, so that an image of the anatomy of the patient to be irradiated is produced. Such imaging is used to align the patient in relation to the therapeutic beam.

A radiation therapy device of this type is disclosed, for example, in U.S. Pat. No. 7,227,925.

SUMMARY AND DESCRIPTION

The present embodiments may obviate one or more of the drawbacks or limitations in the related art. For example, in one embodiment, a radiation therapy device that allows flexible and effective imaging in a simple manner is provided. In another embodiment, a method for flexible and efficient imaging in a radiation therapy device is specified.

The preceding and following description of the individual features relates both to the apparatuses and to the methods; the individual features disclosed in the process and/or apparatuses may also be used in combinations other than those set out.

The radiation therapy device includes: a radiation application apparatus, which may be used to align a therapeutic beam along a therapeutic beam center axis onto a target volume to be irradiated; a diagnostic radiation source for diagnostic x-ray radiation, which is disposed eccentrically in relation to the therapeutic beam center axis in a rotatable manner on a rotation apparatus so that the diagnostic radiation source may be rotated about the therapeutic beam center axis; and a detector for diagnostic x-ray radiation, which may be used to detect the diagnostic x-ray radiation emitted from the diagnostic radiation source.

The radiation application apparatus may be disposed on a rotatable gantry, so that by rotating the gantry (e.g., about an essentially horizontal axis) the direction of the therapeutic beam center axis may be changed. This allows the therapeutic beam to be directed from a number of different directions onto a patient to be irradiated. The diagnostic radiation source is disposed in the radiation therapy device such that by rotating the gantry, the diagnostic radiation source is rotated together with the therapeutic beam center axis. The relative alignment of the diagnostic radiation source to the therapeutic beam center axis or to the radiation application apparatus does not change as a result of rotation of the gantry. This happens if the diagnostic radiation source is rotated about the therapeutic beam center axis. During rotation of the diagnostic radiation source about the therapeutic beam center axis, the radiation application apparatus may remain in the same place spatially. During rotation of the diagnostic radiation source, the relative position of the diagnostic radiation source to the radiation application apparatus or the suspension of the radiation application apparatus (e.g., in relation to the linear accelerator and to the target), from which the therapeutic radiation is directed onto the object, changes.

Radiation therapy devices of the present embodiments allow flexible imaging. The diagnostic radiation source may be rotated about the therapeutic beam center axis, with the result that images of the patient to be irradiated may be produced from different imaging directions. If the target volume would be recorded unfavorably, for example, in one imaging direction (e.g., the target volume would be covered by a bony structure), a different imaging direction, from which an image of the patient is recorded, may be selected in a simple manner. This may also be done with a fixed therapeutic beam center axis. In other words, the gantry is not rotated to obtain different imaging directions for imaging. The eccentrically disposed diagnostic radiation source and the rotation of the diagnostic radiation source, in some instances with corresponding rotation of the radiation detector, allows a different imaging direction to be selected in a simple manner using a fixed therapeutic beam center axis.

In one embodiment, the diagnostic radiation source is disposed in the radiation therapy device such that the angle between the therapeutic beam center axis and the central beam emitted by the diagnostic radiation source is less than 20° (e.g., less than 10°). Images of the patient to be irradiated, which are recorded from an imaging direction that is approximately the same as the therapeutic beam center axis, may be produced. These images are therefore very close to the imaging along the therapeutic beam center axis (e.g., "inline imaging"). This is advantageous, for example, when tracking moving organs, as it is thus easy to track movements perpendicular to the therapeutic beam center axis online.

The diagnostic radiation source may be, for example, a kV radiation source (e.g., the diagnostic radiation source emits x-ray beams that correspond to an x-ray tube voltage of up to several hundred kV and generally less than 150 kV). In contrast, with therapeutic beams, x-ray beams that correspond to a tube voltage of more than 1 MV may be used. Images produced with a diagnostic radiation source may have a better resolution and show the anatomy of a patient better than recordings produced with the therapeutic radiation source.

In one embodiment, the diagnostic radiation source is assigned an aperture apparatus, which may be used to define the lateral extensions of the diagnostic x-ray beam. The aperture apparatus may be rotatable in relation to the x-ray beam emitted by the diagnostic radiation source. This allows the emitted x-ray beam to be defined so that the emitted x-ray beam strikes a radiation detector appropriately, even if the radiation detector has a fixed spatial relationship to the radiation therapy device or the gantry of the radiation therapy device and does not rotate about the therapeutic beam center axis.

In one embodiment, the radiation application apparatus includes a collimator (e.g., a multileaf collimator). The collimator is supported in such a manner that the collimator may be rotated about the therapeutic beam center axis. In this embodiment, the diagnostic radiation source is connected to the rotatably supported collimator or integrated in the rotation apparatus of the rotatably supported collimator. This allows the diagnostic radiation source to be disposed in a space-saving manner in the radiation therapy device while still allowing rotation, since a collimator may already be rotatably supported to set an irradiation field in the desired manner. Also in this embodiment, the aperture apparatus may be integrated in the housing of the collimator, so that the arrangement is space-saving, and a conventional radiation therapy device is modified to a limited degree.

In one embodiment, the radiation therapy device includes a further diagnostic radiation source for diagnostic x-ray radiation. The further diagnostic radiation source is also disposed eccentrically in relation to the therapeutic beam center axis in a rotatable manner on a rotation apparatus so that the diagnostic radiation source may be rotated about the therapeutic beam center axis. The diagnostic radiation source and the further diagnostic radiation source may be disposed on opposing sides in relation to the therapeutic beam center axis. The therapeutic beam center axis may pass through the center point of a putative line between the two radiation sources. Like the first diagnostic radiation source, the further diagnostic radiation source or an assigned aperture apparatus may be connected to the rotatably supported collimator or integrated in the housing of the rotatably supported collimator.

In one embodiment, a control apparatus of the radiation therapy device may activate the diagnostic radiation source and the further diagnostic radiation source simultaneously. This allows images to be produced simultaneously from two different imaging directions, so that three-dimensional spatial information about the anatomical conditions of a patient to be irradiated may be obtained by evaluating the one image and the other image. Using two diagnostic radiation sources produces a greater output, as the x-ray output may be distributed to two radiation sources. Both radiation sources may be activated simultaneously.

In another embodiment, a control apparatus of the radiation therapy device may activate the diagnostic radiation source and/or the further diagnostic radiation source during a rotation of the diagnostic radiation source about the therapeutic beam center axis. The resulting series of images allows an evaluation apparatus to produce a tomosynthesis image. Such an image, even though it is two-dimensional contains detailed information about the three-dimensional anatomy of the patient, as the level of the section through the patient, which corresponds to the tomosynthesis image, is known. This has the advantage of producing a virtually three-dimensional image without having to move the gantry, which is associated with a collision risk for a patient.

In one embodiment, a method for operating a radiation therapy device with a rotatable gantry, on which a radiation application apparatus is disposed, and a diagnostic radiation source for diagnostic x-ray radiation, includes: rotating the gantry about a gantry axis, so that a therapeutic beam center axis is set spatially; and rotating the diagnostic radiation source about the therapeutic beam center axis so that an imaging direction is set.

The radiation therapy device may include a further diagnostic radiation source, and the method may further include rotating the further diagnostic radiation source about the spatially set therapeutic beam center axis.

An image of an object positioned in the radiation therapy device may be produced after rotation of the gantry and after rotation of the diagnostic radiation source, in that, for example, diagnostic x-ray radiation is directed from the radiation source onto a diagnostic radiation detector.

A series of images of an object positioned in the radiation therapy device may also be produced, with the series of images being produced after rotation of the gantry and during rotation of the diagnostic radiation source. With such image quality or the image data obtained with the series of images, a tomosynthesis image may be produced.

BRIEF DESCRIPTION OF THE DRAWINGS

FIG. 5 shows a diagram of yet another embodiment of a method for operating a radiation therapy device.

DETAILED DESCRIPTION OF THE DRAWINGS

Figure 1:
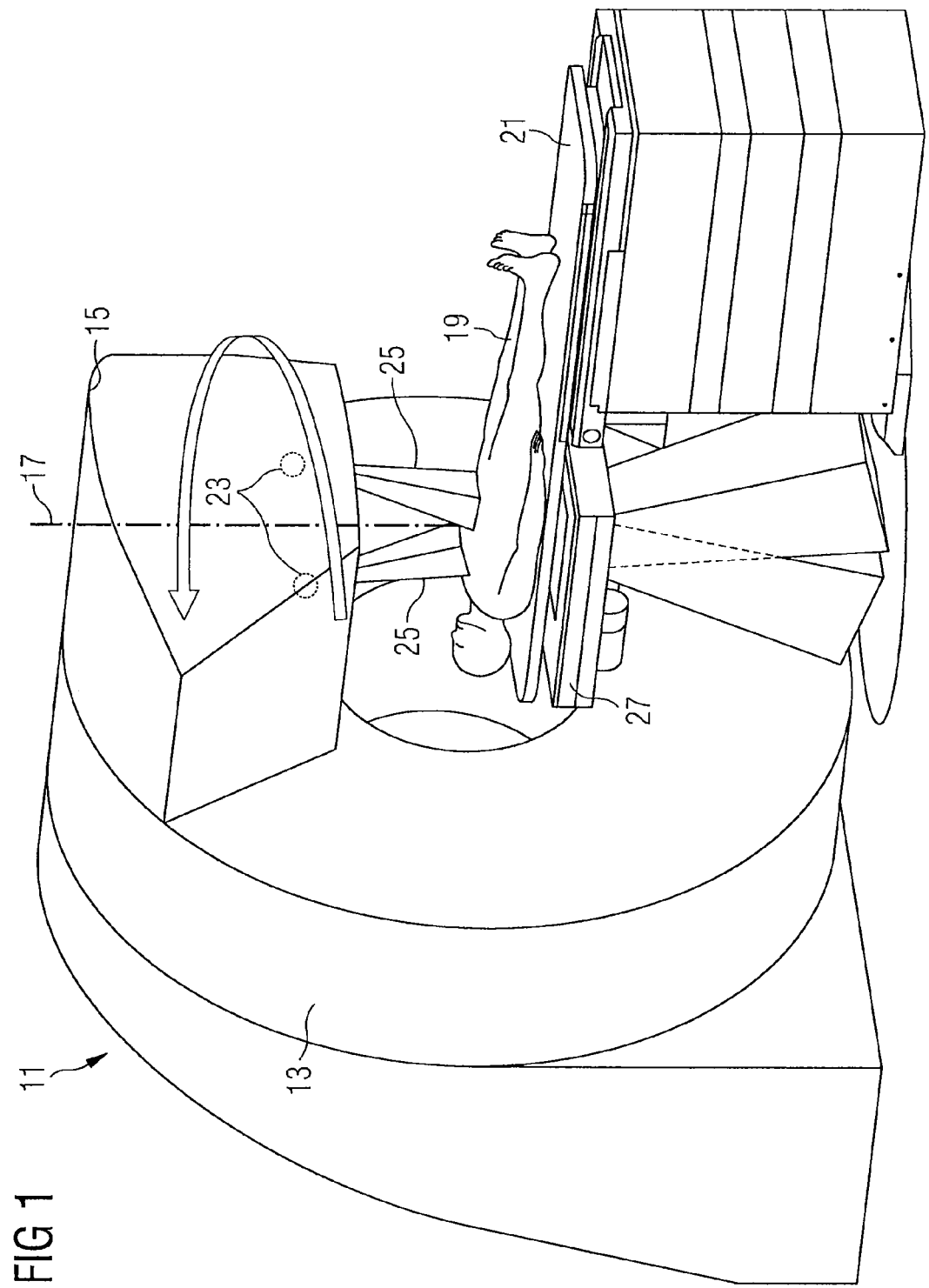
FIG. 1 shows a diagram of one embodiment of a radiation therapy device.

FIG. 1 shows one embodiment of a radiation therapy device 11. The radiation therapy device 11 illustrated in FIG. 1 includes an o-shaped gantry 13. An overhanging arm 15 is secured to the gantry 13 as part of the gantry 13, with parts of an accelerator unit or radiation application apparatus (e.g., a collimator) being integrated in the overhanging arm 15. A therapeutic beam may be directed from the overhanging arm 15 along a therapeutic beam center axis 17 onto a patient 19.

The patient 19 lies on a patient couch 21 that aligns the patient 19 appropriately relative to the therapeutic beam using translatory and/or rotatory movements.

In order to check the correct positioning of the patient 19, the position of the patient 19 is may be monitored with the aid of x-ray imaging before the start of an irradiation session. X-ray imaging may also be employed during irradiation, in order to be able to check or track the position of a target volume.

In the embodiment illustrated in FIG. 1, the radiation therapy device 11 includes two diagnostic radiation sources 23, from which diagnostic x-ray radiation 25 (e.g., an x-ray beam bundle 25) may be directed through the patient onto a detector 27. The two diagnostic radiation sources 23 are disposed in the radiation therapy device 11 such that the two diagnostic radiation sources 23 may be rotated about the therapeutic beam center axis 17.

In the configuration illustrated in FIG. 1, the therapeutic beam center axis 17 runs vertically. By rotating the gantry 13, however, the therapeutic beam center axis 17 may also assume different directions. The two diagnostic radiation sources 23 are carried along in the process so that even if the therapeutic beam center axis 17 is aligned differently, the diagnostic radiation sources 23 may be rotated about the therapeutic beam center axis 17.

The angle formed between the x-ray beam bundle 25 emitted by the radiation sources 23 and the therapeutic beam center axis 17 may be, for example, less than 15°. This allows imaging in the radiation direction of the therapeutic beam, which is helpful, for example, in detecting an organ movement perpendicular to the therapeutic beam, as such organ movements have a greater influence on the correct dose deposition than organ movements in the direction of the therapeutic beam.

The x-ray beams 25 emitted by the diagnostic radiation sources 23 pass through the patient 19 before striking a detector 27, which rotates with the gantry 13 during rotation of the gantry 13.

Figure 2:
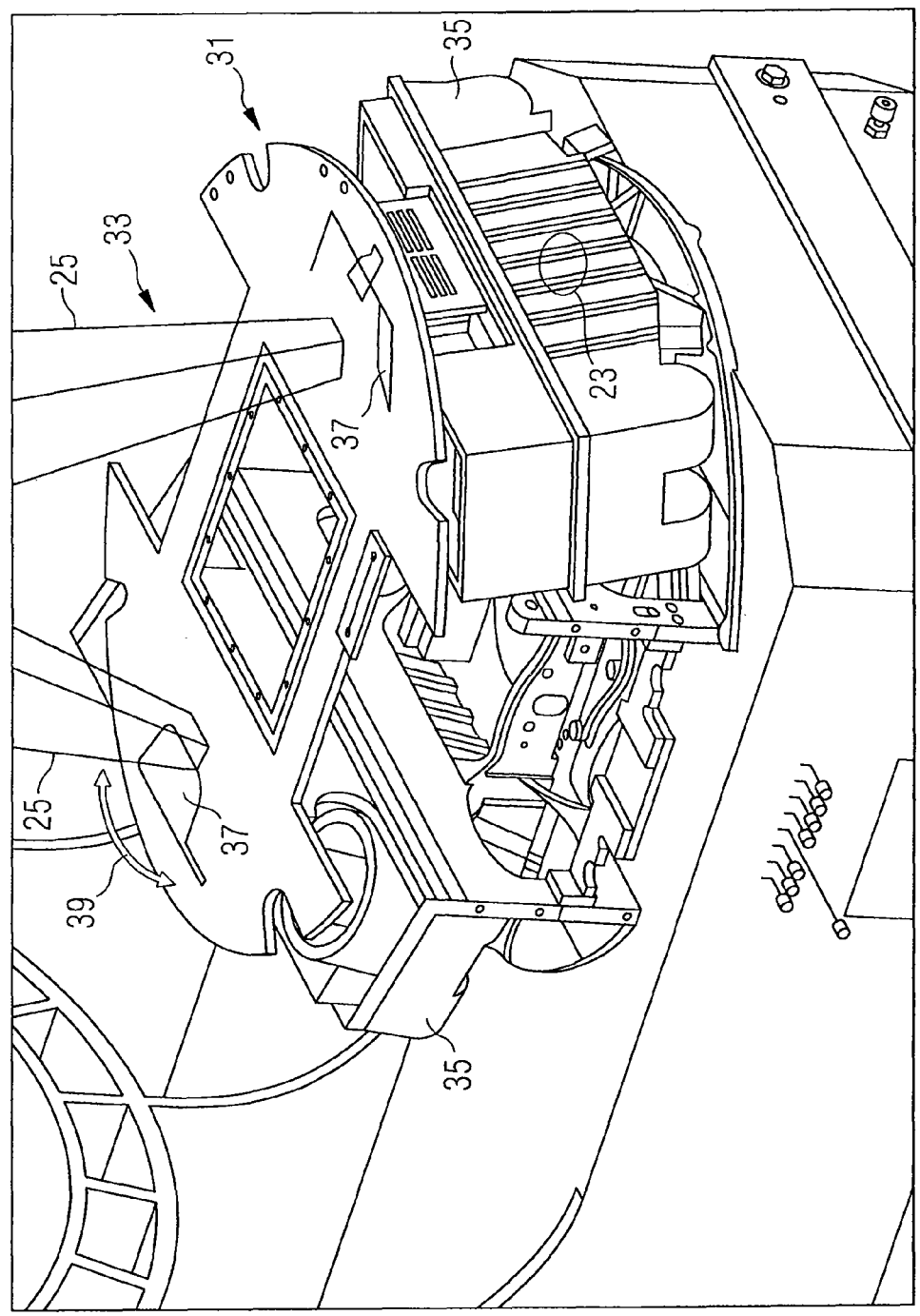
FIG. 2 shows a diagram of one embodiment of diagnostic radiation sources.

FIG. 2 shows a more detailed diagram of one embodiment of the collimator unit 31, which is located in the overhanging arm 15. A cover of the overhanging arm 15 has been removed to show the components more clearly. The collimator unit 31 contains a multileaf collimator 33, which may define the therapeutic beam and tailor the form of the therapeutic beam to the target volume to be irradiated. The multileaf collimator 33 shown in FIG. 2 includes two opposing sets of collimator leaves. The collimator unit 31 is supported such that the collimator unit 31 may be rotated about the therapeutic beam center axis 17.

Integrated in the collimator unit 31 are two single tanks 35, which contain the radiation sources 23 for the diagnostic x-ray radiation 25. One single tank 35 is located on one side of a set of collimator leaves.

Also integrated in the collimator unit 31 is an aperture apparatus 37 for the diagnostic radiation sources 23. The aperture apparatus 37 is used to define the x-ray beam bundle 25 emitted by the radiation sources 23. The aperture apparatus 37 may be rotated in relation to the x-ray beam bundle 25, as shown by the double arrow 39, so that the x-ray beam bundle 25 may be defined so that the form of the x-ray beam bundle 25 is tailored to the detector 27 even during rotation of the diagnostic radiation sources 23. The x-ray beam bundle may be defined, for example, such that the beam bundle 25 always strikes the permanently aligned detector 27 orthogonally.

Rotation of the collimator unit 31, therefore, brings about both the rotation of the multileaf collimator 33 and the rotation of the diagnostic radiation sources 23 about the therapeutic beam center axis 17. The housing of the diagnostic radiation sources 23 in the collimator unit 31 also allows the radiation sources 23 to be brought as close as possible to the therapeutic beam center axis 17.

Figure 3:
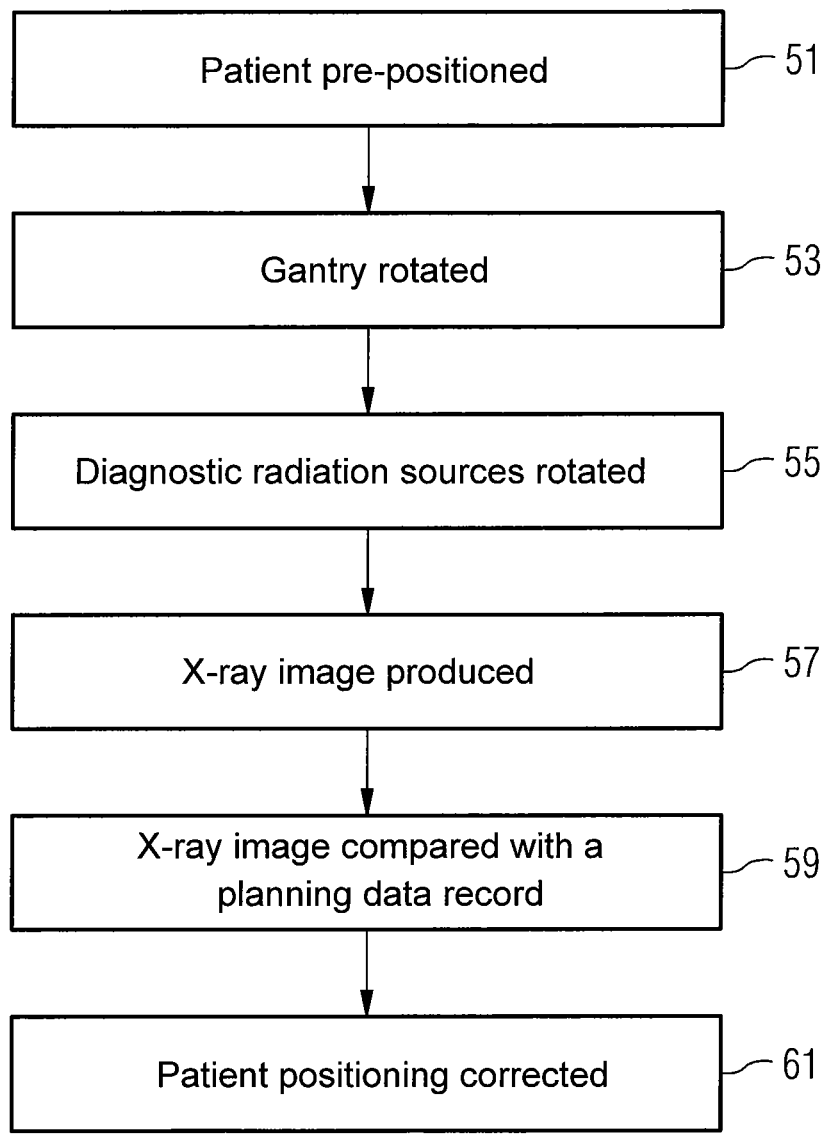
FIG. 3 show a diagram of one embodiment of a method for operating a radiation therapy device.

FIG. 3 shows a schematic flow diagram of one embodiment of a method that may be carried out using a radiation therapy device as described above.

In method act 51, a patient is positioned in a radiation therapy device.

A gantry is rotated about a horizontal axis to align a therapeutic beam center axis as planned (act 53).

In a further act, a diagnostic radiation source is rotated about the therapeutic beam center axis in order to be moved into a position advantageous for imaging (act 55). Interfering bony structures overlaying the target volume, for example, may be prevented.

An x-ray image of the patient is produced (act 57). The x-ray image is compared with a planning data record that forms the basis for therapy planning (act 59) to determine whether the target volume is in a desired position or whether the position is to be corrected (act 61).

Figure 4:
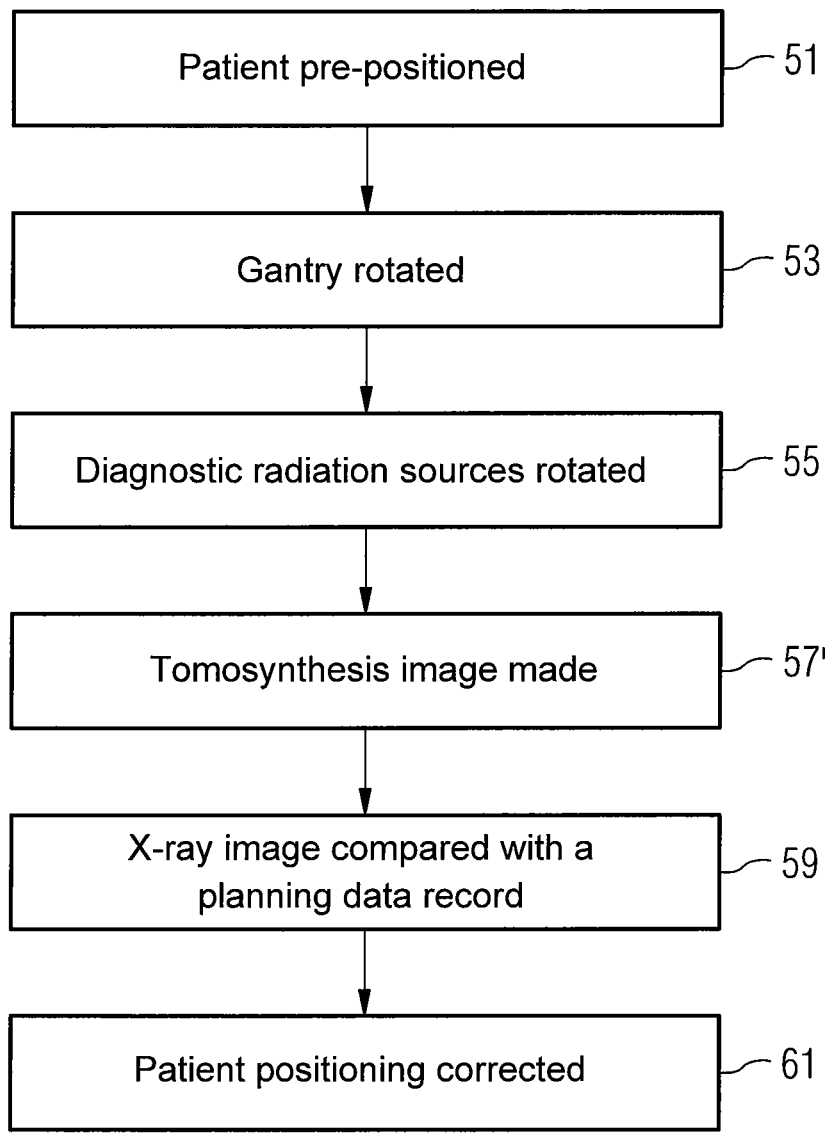
FIG. 4 shows a diagram of another embodiment of a method for operating a radiation therapy device.

FIG. 4 shows a schematic flow diagram of one embodiment of a method for operating a radiation therapy device.

In contrast to the method shown in FIG. 3, a series of diagnostic x-ray images is produced (act 57') during rotation of the diagnostic radiation sources about the therapeutic beam center axis (act 55). The series of images is used to reconstruct a tomosynthesis image, which shows a section through the target volume.

This sectional image is compared with the planning data record that forms the basis for therapy planning (act 59) in order to optionally correct the position of the patient (act 61).

FIG. 5 is different from FIG. 3 and FIG. 4 such that in act 57 or act 57', a stereoscopic image is produced by the two diagnostic radiation sources 23 (act 57") and is used to monitor the position of the target volume.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A radiation therapy device comprising:
a radiation application apparatus that is operable to direct a therapeutic beam along a therapeutic beam center axis onto a target volume to be irradiated;
a diagnostic radiation source for diagnostic x-ray radiation, the diagnostic radiation source being disposed eccentrically in relation to the therapeutic beam center axis in a rotatable manner on a rotation apparatus so that the diagnostic radiation source is operable to be rotated about the therapeutic beam center axis; and
a detector for diagnostic x-ray radiation that is operable to detect the diagnostic x-ray radiation emitted from the diagnostic radiation source,
wherein the radiation application apparatus is disposed on a rotatable gantry so that by rotating the gantry, a direction of the therapeutic beam center axis is changed,
wherein the diagnostic radiation source is disposed in the radiation therapy device such that by rotating the gantry, the diagnostic radiation source is rotated together with the therapeutic beam center axis, and
wherein the diagnostic radiation source is operable to be rotated about the therapeutic beam center axis, such that an imaging direction is changeable without rotating the gantry.

2. The radiation therapy device as claimed in claim 1, wherein the diagnostic radiation source is assigned an aperture apparatus that is operable to define lateral extensions of the diagnostic x-ray radiation.

3. The radiation therapy device as claimed in claim 1, wherein the radiation application apparatus comprises a collimator that is supported such that the collimator is operable to be rotated about the therapeutic beam center axis, and
wherein the diagnostic radiation source is connected to the rotatably supported collimator.

4. The radiation therapy device as claimed in claim 1, comprising a further diagnostic radiation source for diagnostic x-ray radiation, the further diagnostic radiation source being disposed eccentrically in relation to the therapeutic beam center axis in a rotatable manner on the rotation apparatus so that the further diagnostic radiation source is operable to be rotated about the therapeutic beam center axis.

5. The radiation therapy device as claimed in claim 4, wherein the therapeutic beam center axis passes through a center point between the diagnostic radiation source and the further diagnostic radiation source.

6. The radiation therapy device as claimed in claim 4, wherein the diagnostic radiation source and the further diagnostic radiation source are operable to be activated simultaneously.

7. The radiation therapy device as claimed in claim 1, wherein the diagnostic radiation source is operable to be activated during rotation of the diagnostic radiation source about the therapeutic beam center axis.

8. The radiation therapy device as claimed in claim 7, further comprising an evaluation apparatus for reconstructing a tomosynthesis image from image data generated by the rotating diagnostic radiation source.

9. The radiation therapy device as claimed in claim 1, wherein the diagnostic radiation source is disposed in the radiation therapy device such that an angle between the therapeutic beam center axis and a central beam emitted by the diagnostic radiation source is less than 20°.

10. The radiation therapy device as claimed in claim 9, wherein the diagnostic radiation source is disposed in the radiation therapy device such that the angle between the therapeutic beam center axis and a central beam emitted by the diagnostic radiation source is less than 10°.

11. The radiation therapy device as claimed in claim 2, comprising a further diagnostic radiation source for diagnostic x-ray radiation, the further diagnostic radiation source being disposed eccentrically in relation to the therapeutic beam center axis in a rotatable manner on the rotation apparatus so that the further diagnostic radiation source is operable to be rotated about the therapeutic beam center axis.

12. The radiation therapy device as claimed in claim 2, wherein the diagnostic radiation source is operable to be activated during rotation of the diagnostic radiation source about the therapeutic beam center axis.

13. A method for operating a radiation therapy device having a rotatable gantry, on which a radiation application apparatus that is operable to direct a therapeutic beam along a therapeutic beam center axis is disposed, and a diagnostic radiation source for diagnostic x-ray radiation, the method comprising:

rotating the gantry about a gantry axis, so that an orientation of the therapeutic beam center axis is set; and rotating the diagnostic radiation source about the therapeutic beam center axis without additional rotation of the gantry so that an imaging direction is set.

14. The method as claimed in claim 13, wherein the radiation therapy device comprises a further diagnostic radiation source, and wherein the method further comprises rotating the further diagnostic radiation source about the spatially set therapeutic beam center axis.

15. The method as claimed in claim 14, further comprising producing an image of an object positioned in the radiation therapy device after rotating the diagnostic radiation source about the therapeutic beam center axis.

16. The method as claimed in claim 14, further comprising producing a series of image data of an object positioned in the radiation therapy device during rotation of the diagnostic radiation source about the therapeutic beam center axis.

17. The method as claimed in claim 13, further comprising producing an image of an object positioned in the radiation therapy device after rotating the diagnostic radiation source about the therapeutic beam center axis.

18. The method as claimed in claim 13, further comprising producing a series of image data of an object positioned in the radiation therapy device during rotation of the diagnostic radiation source about the therapeutic beam center axis.

19. The method as claimed in claim 18, further comprising producing a tomosynthesis image from the series of image data.

* * * * *